(12) United States Patent
Dejima et al.

(10) Patent No.: US 10,945,711 B2
(45) Date of Patent: *Mar. 16, 2021

(54) TISSUE SAMPLING DEVICE

(71) Applicant: FUJIFILM Corporation, Tokyo (JP)

(72) Inventors: Takumi Dejima, Kanagawa (JP);
Masayuki Iwasaka, Kanagawa (JP);
Shinichi Yamakawa, Kanagawa (JP);
Manabu Miyamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

This patent is subject to a terminal disclaimer.

(21) Appl. No.: 14/951,499

(22) Filed: Nov. 25, 2015

(65) Prior Publication Data

US 2016/0074021 A1 Mar. 17, 2016

Related U.S. Application Data

(63) Continuation of application No. PCT/JP2017/063654, filed on May 23, 2014.

(30) Foreign Application Priority Data

May 27, 2013 (JP) ............................... JP2013-111162

(51) Int. Cl.
*A61B 10/02* (2006.01)
*A61B 8/08* (2006.01)
(Continued)

(52) U.S. Cl.
CPC ........ *A61B 10/0266* (2013.01); *A61B 8/0841* (2013.01); *A61B 8/12* (2013.01); *A61B 1/04* (2013.01); *A61B 2010/045* (2013.01)

(58) Field of Classification Search
None
See application file for complete search history.

(56) References Cited

U.S. PATENT DOCUMENTS 5,928,162 A 7/1999 Giurtino et al.
6,015,381 A 1/2000 Ouchi
(Continued)

FOREIGN PATENT DOCUMENTS

IE S77150 11/1997
JP S52040615 9/1977
(Continued)

OTHER PUBLICATIONS

"The Extended European Search Report of European Counterpart Application", dated May 2, 2016, pp. 1-7.
(Continued)

*Primary Examiner* — Patrick Fernandes
*Assistant Examiner* — Benjamin S Melhus
(74) *Attorney, Agent, or Firm* — JCIPRNET

(57) ABSTRACT

A tissue sampling device includes a flexible sheath 34; a needle tube 35 which is inserted into the sheath 34 so as to advance and retreat and with which biological tissue is punctured; and an operating unit which is provided on a proximal side of the sheath 34 and is used for operating the advancing and retreating of the needle tube 35. This needle tube 35 has a distal portion provided with a slit 50 extending toward the proximal side from a distal opening 35*c*, and when the distal portion is in a state of protruding from a distal end of the sheath 34, at least a part of the distal portion is positioned further on the radially outside than the inner surface of the sheath when viewed from an axial direction of the needle tube 35.

4 Claims, 15 Drawing Sheets

(51) Int. Cl.
  *A61B 8/12* (2006.01)
  *A61B 10/04* (2006.01)
  *A61B 1/04* (2006.01)

(56) References Cited

U.S. PATENT DOCUMENTS

| | | | | |
|---|---|---|---|---|
| 6,063,037 | A * | 5/2000 | Mittermeier | A61B 10/025 600/567 |
| 6,086,543 | A | 7/2000 | Anderson et al. | |
| 6,569,151 | B1 * | 5/2003 | Nash | A61M 25/00 604/103 |
| 6,755,793 | B2 * | 6/2004 | Lamoureux | A61B 10/025 600/567 |
| 6,872,192 | B2 * | 3/2005 | Nash | A61M 25/00 604/158 |
| 2006/0235334 | A1 * | 10/2006 | Corvi | A61B 10/04 600/564 |
| 2007/0055215 | A1 * | 3/2007 | Tran | A61B 10/0275 604/540 |
| 2007/0185416 | A1 * | 8/2007 | Melsheimer | A61M 25/09 600/585 |
| 2007/0213634 | A1 | 9/2007 | Teague | |
| 2008/0132930 | A1 * | 6/2008 | Lubock | A61B 10/0275 606/171 |
| 2008/0234699 | A1 | 9/2008 | Oostman, Jr. et al. | |
| 2009/0287114 | A1 * | 11/2009 | Lee | A61B 10/0266 600/566 |
| 2012/0197157 | A1 * | 8/2012 | Ryan | A61B 10/0266 600/567 |
| 2012/0245487 | A1 | 9/2012 | Eells et al. | |
| 2013/0158429 | A1 * | 6/2013 | Lee-Sepsick | A61B 10/04 600/570 |
| 2015/0073299 | A1 * | 3/2015 | Vetter | A61B 17/32002 600/564 |
| 2016/0081678 | A1 * | 3/2016 | Kappel | A61B 10/0233 600/567 |

FOREIGN PATENT DOCUMENTS

| | | |
|---|---|---|
| JP | S62-261355 | 11/1987 |
| JP | H103019847 | 4/1991 |
| JP | 10192286 | 7/1998 |
| JP | 2000232983 | 8/2000 |
| JP | 2002-95749 | 4/2002 |
| JP | 2005-73798 | 3/2005 |
| JP | 3661470 | 6/2005 |
| WO | 2011136719 | 11/2011 |
| WO | 2011139876 | 11/2011 |

OTHER PUBLICATIONS

"Office Action of Japan Counterpart Application" with English translation thereof, dated Aug. 19, 2016, p. 1-p. 6.

"PCT/IB/373:International Preliminary Report on Patentability" dated Dec. 1, 2015, including "PCT/ISA/237:Written Opinion of the International Searching Authority of PCT/JP2014/063654", which is English translation of "PCT/ISA237:Written Opinion of the International Searching Authority", pp. 1-11.

"Written Opinion of the International Searching Authority of PCT/JP2014/050556", this report contains the following items: Form PCT/ISA237(cover sheet), PCT/ISA237(Box No. 1), PCT/ISA237(Box No. V), dated Mar. 18, 2014, which is English translation of "Written Opinion of the International Searching Authority", pp. 1-9.

"Office Action of Japan Counterpart Application" with English translation, dated Jun. 7, 2016, p. 1-p. 6.

"The Extended European Search Report of European Counterpart Application", dated Jan. 28, 2016, pp. 1-7.

"Office Action of Co-pending U.S. Appl. No. 14/800,703", dated Oct. 24, 2016, p. 1-p. 26.

"Office Action of Co-pending U.S. Appl. No. 14/800,703", dated Apr. 11, 2017, p. 1-p. 10.

"Office Action of Co-pending U.S. Appl. No. 14/800,703", dated Aug. 25, 2017, p. 1-p. 4.

"Office Action of Co-pending U.S. Appl. No. 14/800,703", dated Oct. 31, 2017, p. 1-p. 20.

* cited by examiner

TISSUE SAMPLING DEVICE

CROSS-REFERENCE TO RELATED APPLICATIONS

The present application is a Continuation of PCT International Application No. PCT/JP2014/063654 filed on May 23, 2014 claiming priority under 35 U.S.C § 119(a) to Japanese Patent Application No. 2013-111162 filed on May 27, 2013. Each of the above applications is hereby expressly incorporated by reference, in their entirety, into the present application.

BACKGROUND OF THE INVENTION

1. Field of the Invention

The present invention relates to a tissue sampling device, and particularly to a tissue sampling device used for sampling biological tissue.

2. Description of the Related Art

In recent years, diagnosis for a pathological confirmation is performed by introducing a puncture needle into a body cavity through a treatment tool insertion channel of an ultrasonic endoscope; guiding a needle tube, which constitutes a puncture needle, to an observation site under ultrasonic tomographic image observation using the ultrasonic endoscope to puncture a lesion tissue; and sampling the biological tissue.

As a tissue sampling device which is used for performing such diagnosis for a pathological confirmation, a tissue sampling device including a flexible sheath which can be freely inserted into a treatment tool insertion channel of an endoscope; a needle tube (puncture needle) which is inserted into the sheath so as to advance and retreat and with which biological tissue is punctured; and an operating unit which is connected to a proximal portion of the sheath and is used for operating the advancing and retreating of the needle tube, is known as disclosed in, for example, JP2005-73798A.

SUMMARY OF THE INVENTION

In general, there are two types of diagnoses for a pathological confirmation: cytological diagnosis and histological diagnosis. In the cytological diagnosis, every single cell is examined for diagnosis. Therefore, it is difficult to determine whether a test substance is benign or malignant and it is difficult to obtain information up to the diagnosis for a pathological confirmation. In contrast, the histological diagnosis is a method in which one mass in which biological tissues are gathered is wholly examined for diagnosis. Therefore, enough information for performing the diagnosis for a pathological confirmation can be easily obtained. Accordingly, when performing the diagnosis for a pathological confirmation, a sufficient amount of biological tissue for performing the histological diagnosis is desirably sampled.

However, in the tissue sampling device in the related art as disclosed in JP2005-73798A, the needle tube which is led into a body cavity through a treatment tool insertion channel of an endoscope is a thin needle tube of which the diameter is, for example, less than 1 mm. Therefore, in a structure in which biological tissue is taken into the needle tube from a distal opening, the amount of biological tissue which can be sampled through piercing the biological tissue with a sharp edge of the needle tube which is formed at a distal end of the needle tube, is extremely small, and therefore, it is difficult to sample a sufficient amount of biological tissue. For this reason, in a case where the amount of biological tissue sampled is insufficient, puncturing of biological tissue with the needle tube needs to be performed plural times for sampling, and the operation becomes complicated.

In contrast, it is considered that the amount of biological tissue sampled is increased by enlarging the outer diameter of the needle tube constituting the puncture needle. However, there is a limit in increasing the diameter of the needle tube since the diameter thereof is restricted by the treatment tool insertion channel of the endoscope, and therefore, it is difficult to increase the amount of tissue sampled. In addition, if the diameter of the needle tube is increased, it is difficult to avoid increase in stiffness of the needle tube, and therefore, an operation for leading the needle tube, which is led into a body cavity through the treatment tool insertion channel of the endoscope, to an observation site becomes difficult.

The present invention has been made from the viewpoint of such problems, and an object of the present invention is to provide a tissue sampling device which can easily sample a sufficient amount of biological tissue for performing diagnosis for a pathological confirmation.

In order to achieve the above-described purpose, according to the present invention, there is provided a tissue sampling device including: a flexible sheath; a needle tube which is inserted into the sheath so as to advance and retreat and with which biological tissue is punctured; and an operating unit which is provided on a proximal side of the sheath and is used for operating the advancing and retreating of the needle tube. The needle tube has a distal portion provided with a slit extending toward the proximal side from a distal opening, and when the distal portion is in a state of protruding from a distal end of the sheath, at least a part of the distal portion is positioned further on the radially outside than the inner surface of the sheath when viewed from an axial direction of the needle tube.

In an aspect of the tissue sampling device according to the present invention, the distal portion of the needle tube is biased in a direction in which the curvature radius of at least one of edge portions facing each other across the slit is enlarged.

In an aspect of the tissue sampling device according to the present invention, the proximal side of the slit is formed in a spiral shape with respect to the axial direction of the needle tube.

In an aspect of the tissue sampling device according to the present invention, a plurality of the slits are provided in the distal portion of the needle tube.

In an aspect of the tissue sampling device according to the present invention, the slit extends toward the proximal side from a portion other than a sharp tip portion of the distal opening of the needle tube.

In an aspect of the tissue sampling device according to the present invention, the slit extends toward the proximal side from a sharp tip portion of the distal opening of the needle tube.

In an aspect of the tissue sampling device according to the present invention, the diameter of the distal portion of the needle tube is made to be less than or equal to the inner diameter of the sheath when the distal portion thereof is accommodated in the sheath.

According to the present invention, the slit extending toward the proximal side from the distal opening is provided in the distal portion of the needle tube, and when the distal portion of the needle tube protrudes from the distal end of the sheath, at least a part of the distal portion of the needle tube is positioned further on the radially outside than the inner surface of the sheath. Therefore, it is possible to increase the volume of the lumen for taking biological tissue thereinto. Accordingly, it is possible to easily sample a sufficient amount of biological tissue for performing diagnosis for a pathological confirmation.

DESCRIPTION OF THE PREFERRED EMBODIMENT

Hereinafter, a preferred embodiment will be described in detail in accordance with the accompanying drawings.

A tissue sampling device for puncturing to which the present invention is applied is described as a tissue sampling device which is constituted so as to be inserted into a body cavity through a treatment tool insertion channel formed in an ultrasonic endoscope for performing electronic convex scanning. As means for guiding the tissue sampling device, a scanning type ultrasonic endoscope other than the electronic convex scanning type ultrasonic endoscope, a treatment tool insertion channel of a general endoscope which is not provided with an ultrasonic diagnostic mechanism, a trocar, or the like can be used. In a case of inserting a tissue sampling device into a trocar, it is possible to form the entirety of the tissue sampling device with a hard material.

Figure 1:
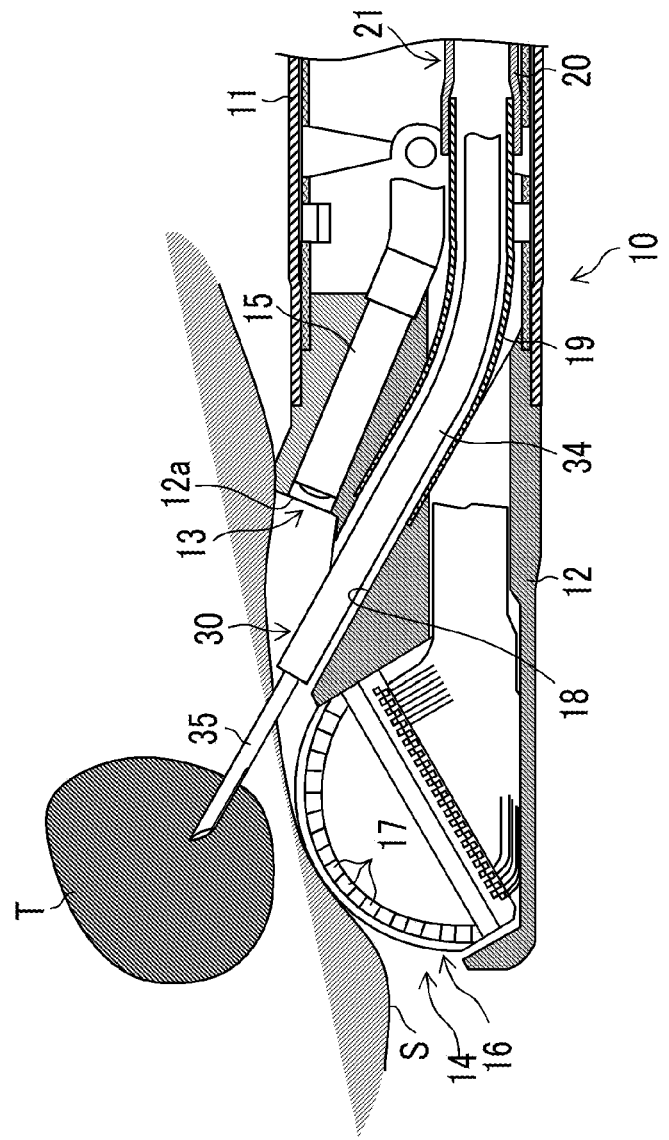
FIG. 1 is a main-portion cross-sectional view showing a state in which a tissue sampling device as an embodiment of the present invention is incorporated into a ultrasonic endoscope.

First, a configuration of a distal portion of an ultrasonic endoscope guiding a tissue sampling device is shown in FIG. 1. In the drawing, 10 represents an insertion unit inserted into a body cavity. This insertion unit 10 is formed by consecutively connecting a distal portion main body 12 to a distal end of an angle portion 11. The distal portion main body 12 is provided with an endoscopic observation portion 13 on a proximal side thereof and with an ultrasonic observation portion 14 on a distal side thereof. The endoscopic observation portion 13 is formed of a section which is provided in an inclination portion 12a on the proximal side of the distal portion main body 12 and faces an observation visual field diagonally forwardly.

An illumination mechanism 15 which is provided with a light guide constituting the endoscopic observation portion 13 is shown in FIG. 1. An observation mechanism is also provided together with the illumination mechanism 15, but is omitted from the drawing. As the observation mechanism, a solid-state imaging element or an image guide is used.

The ultrasonic observation portion 14 has an ultrasonic transducer unit 16 which is installed in an opening portion 12b provided at a distal end of the distal portion main body 12. This ultrasonic transducer unit 16 is used for performing electronic convex scanning and is formed by arranging multiple striped ultrasonic oscillators 17 in a circular arc shape.

A treatment tool lead-out portion 18 is formed at a position between the endoscopic observation portion 13 and the ultrasonic observation portion 14. This treatment tool lead-out portion 18 is a path with a predetermined inner diameter which is bored in the distal portion main body 12 and a connection pipe 19 is connected to this treatment tool lead-out portion 18. This connection pipe 19 is bent at a predetermined angle, and a flexible tube 20 is connected to a proximal portion of the connection pipe. Accordingly, a treatment tool insertion channel 21 is constituted by the treatment tool lead-out portion 18, the connection pipe 19, and the flexible tube 20. The treatment tool lead-out portion 18 extends in an obliquely forward direction with respect to an axial line of the insertion unit 10. The flexible tube 20 extends in an axial direction of the insertion unit 10. An intermediate portion of the connection pipe 19 is bent by a predetermined angle.

30 is a tissue sampling device. This tissue sampling device 30 is designed so as to come in and out of this treatment tool lead-out portion 18 by being inserted into the treatment tool insertion channel 21. Therefore, the distal portion main body 12 is made to abut on a body cavity inner wall S, biological tissue sampling site T is put into an ultrasonic observation visual field using the ultrasonic observation portion 14, the body cavity inner wall S is pierced with a distal end of the tissue sampling device 30 from the treatment tool lead-out portion 18, and the distal end thereof is led to the tissue sampling site T. Then, it is possible to sample the biological tissue.

Figure 2:
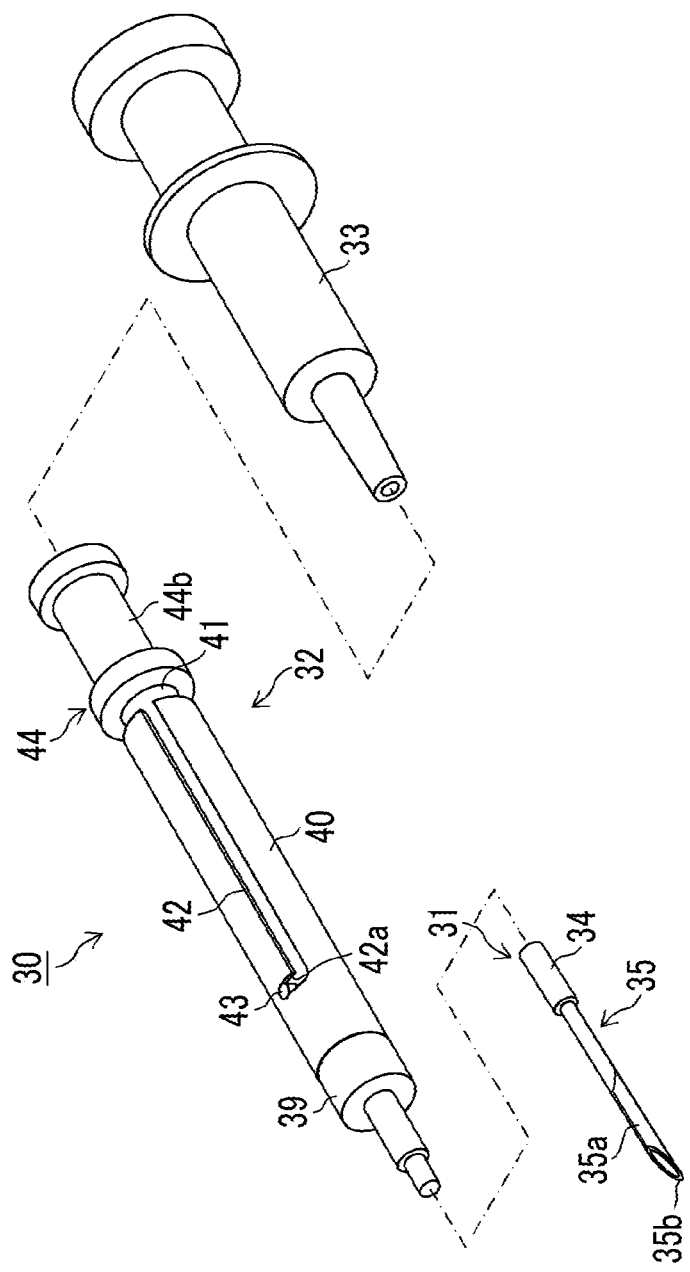
FIG. 2 is an overall constitution view of the tissue sampling device.

An overall configuration of the tissue sampling device 30 is shown in FIG. 2. As shown in FIG. 2, the tissue sampling device 30 is constituted of an insertion unit 31 and an operating unit 32, and a syringe 33 is detachably connected to a proximal portion of the operating unit 32.

Figure 3:
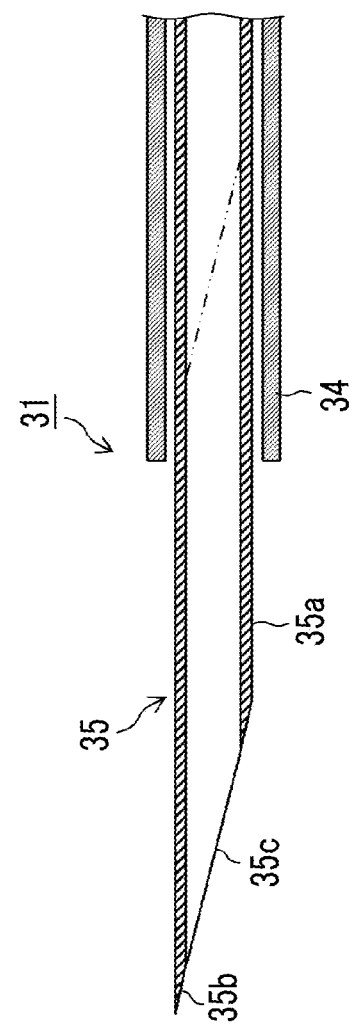
FIG. 3 is a cross-sectional view of a distal portion of an insertion unit constituting the tissue sampling device.

The length of the insertion unit 31 is longer than at least the whole length of the treatment tool insertion channel 21, and the insertion unit 31 is formed of double cylindrical members as shown in FIG. 3. That is, the insertion unit 31 is constituted of a sheath 34 and a needle tube 35 which is inserted into this sheath 34, from the outermost peripheral side.

The sheath 34 is designed to be inserted into a treatment tool insertion channel of an endoscope and constitutes the exterior of the insertion unit 31. The sheath 34 is formed of a cylindrical member having flexibility and is formed of, for example, a resin material such as polyethersulfone or Teflon (registered trademark). In addition, the sheath 34 may be formed of a tightly wound coil or the like.

The needle tube 35 is designed to sample a lesion tissue or the like which has been obtained by puncturing biological tissue, and is inserted into and disposed in the sheath 34 so as to advance and retreat. In this needle tube 35, a distal end of a thin pipe-like main body pipe 35a is opened and the distal portion thereof is obliquely cut. Accordingly, a needle tip 35b is formed as a sharp tip portion of which a distal end is pointed. In addition, the needle tube 35 is formed of a hard member and at least the distal portion including the needle tip 35b needs to be made hard since the needle tube is punctured into the body.

Here, since the insertion unit 31 is inserted into the treatment tool insertion channel 21, the insertion unit needs to have flexibility in a bending direction in order to make the insertion unit pass the bent connection pipe 19 and make the insertion unit be smoothly inserted thereinto even in a state in which the angle portion 11 is curved. For this reason, a site other than the distal portion including the needle tip 35b of the needle tube 35 may be configured so as to connect a flexible tube and a hard pipe by being formed of the tube. However, the needle tube 35 has a thin diameter and can be bent if the thickness of the needle tube is made to be as thin as possible, and therefore, the entire length of the needle tube 35 is formed of a pipe member made of metal or the like.

The needle tube 35 is designed to be movable in the sheath 34 in a back and forth direction and moves between a retreating position (position shown by a virtual line in FIG. 3) at which the needle tip 35b thereof is covered by the sheath 34 and an operating position (position shown by a solid line in FIG. 3) at which the needle tip protrudes from the distal end of the sheath 34 by a predetermined length.

Figure 4:
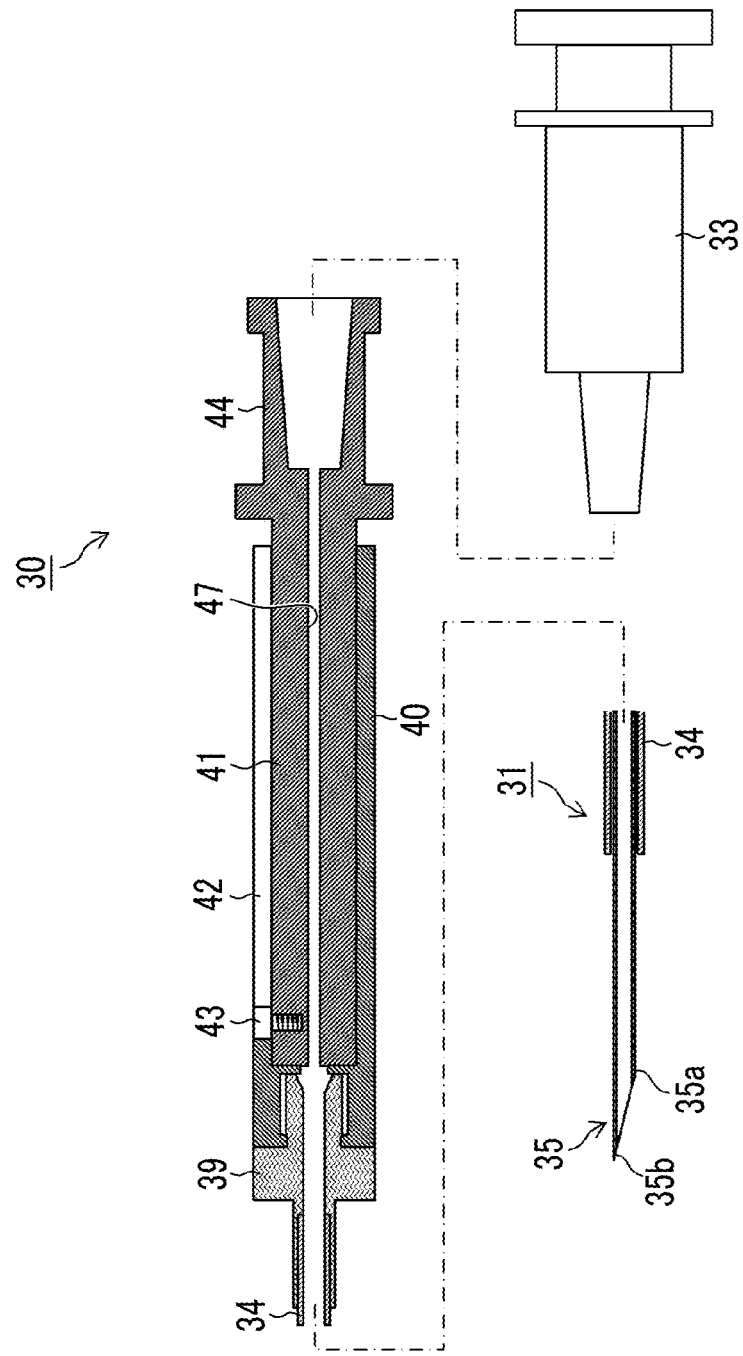
FIG. 4 is a cross-sectional view of the tissue sampling device.

For this reason, the proximal portion of the sheath 34 is connected to the operating unit 32 which is operated such that the needle tube 35 is made to come in and out of the distal end of the sheath 34. A specific configuration of the operating unit 32 is as shown in FIG. 4.

The proximal portion of the sheath 34 is fixed to a connecting member 39 which is connected to a casing 40. The casing 40 is formed of a cylindrical member having a predetermined length and into which a slider 41 is slidably inserted in an axial direction. The slider 41 is made to be hollow and the proximal portion of the needle tube 35 is fixed to the inside of the slider 41. Accordingly, when an operation of pushing/pulling the slider 41 is performed, the needle tip 35b at the distal end of the needle tube 35 comes in and out of the distal end of the sheath 34.

In addition, a guide hole 42 with a predetermined length is provided in a peripheral body portion of the casing 40 in an axial direction and a pin 43 which is inserted into the guide hole 42 is attached to the slider 41. A distal end of the guide hole 42 is a positioning hole portion 42a by being bent by approximately 90° and facing a circumferential direction. The rear end of the guide hole 42 extends up to the rear end of the casing 40.

A state in which the slider 41 is drawn from the casing 40 and the needle tube 35 is drawn into the sheath 34 is a state in which the needle tube 35 is at a retreating position. If the state of the pin 43 is shifted to a state in which the pin 43 is taken out of the rear end of the guide hole 42, for example, a state in which the pin 43 is made to abut on the rear end (section which is not provided with the guide hole 42) of the casing 40, the needle tube 35 can be held at this retreating position. In the retreating position, the needle tip 35b of the needle tube 35 is positioned slightly inside the distal end of the sheath 34 and enters a state of being completely covered by the sheath 34. Therefore, when inserting the sheath into the treatment tool insertion channel 21 or the like, there is no case where other objects are punctured with or caught by the needle tip 35b. Thus, stability is secured and the operation of inserting the sheath into the treatment tool insertion channel 21 is smoothly performed. If the pin 43 is in a state in which the slider 41 is further drawn from the casing 40 more than the state in which the pin 43 abuts on the rear end of the casing 40, that is, if the pin 43 is in a state of not being engaged with the guide hole 42, the needle tube 35 enters a state of being completely covered by the sheath 34. The position of the needle tube 35 in this state also becomes the retreating position.

In contrast, when the slider 41 is pushed into the casing 40 while engaging the pin 43 with the guide hole 42, the needle tube 35 is led out from the sheath 34. When the pin 43 is disposed at a position at which the pin is engaged with the positioning hole portion 42a at the distal end of the guide hole 42, the needle tube 35 protrudes from the sheath 34 by a predetermined length. This position is an operating position which the needle tube can puncture, and the protrusion length at this operating position becomes a maximum piercing length into the body.

Here, the maximum piercing length of the needle tube 35 is a length in which the needle tube 35 is pierced up to a position at which the sheath 34 abuts on a body cavity inner wall. Even in this state, it is necessary to make the needle tip 35b enter the ultrasonic observation visual field using the ultrasonic transducer unit 16. Accordingly, the maximum piercing length of the needle tube 35 is restricted to the ultrasonic observation visual field.

In order to shift the pin 43 which is provided on the slider 41 side at the above-described operating position to the positioning hole portion 42a from the guide hole 42 of the casing 40 and to stabilize the pin at the position, the casing 40 and the slider 41 may be relatively rotated. Furthermore, if the width of the transition portion from the guide hole 42 to the positioning hole portion 42a is made to be slightly narrower than the outer diameter dimension of the pin 43, a click feeling can be obtained during the transition and the pin 43 can be stably held. In order to stabilize the slider 41 at the above-described retreating position, the casing 40 and the slider 41 may be relatively rotated such that the pin 43 which has been removed from the guide hole 42 is not easily engaged with the guide hole 42, so as to move the pin 43 to a position at which the pin is retreated from the axial line of the guide hole 42. Furthermore, if the width of the vicinity of the rear end of the guide hole 42 is made to be slightly narrower than the outer diameter dimension of the pin 43, a click feeling can be obtained during the transition of the slider 41 to the retreating position and the slider 41 can be stably held at the retreating position even if the pin 43 is not retreated from the axial line of the guide hole 42.

The needle tube 35 also functions as a fluid path. This fluid path acts as a suction path for applying negative pressure and a path for feeding a fluid such as a formalin liquid in order to discharge tissue which has been accommodated in the needle tube 35. A flow path 47 is formed in the slider 41 as an extension portion of the fluid path in the needle tube 35. The proximal portion of this slider 41 is set to a luer lock portion 44, to which syringes 33 for suction and for feeding a liquid are detachably connected.

Next, the configuration of the distal portion of the insertion unit 31 which is a characteristic portion of the present invention will be described in detail.

Figure 5A:
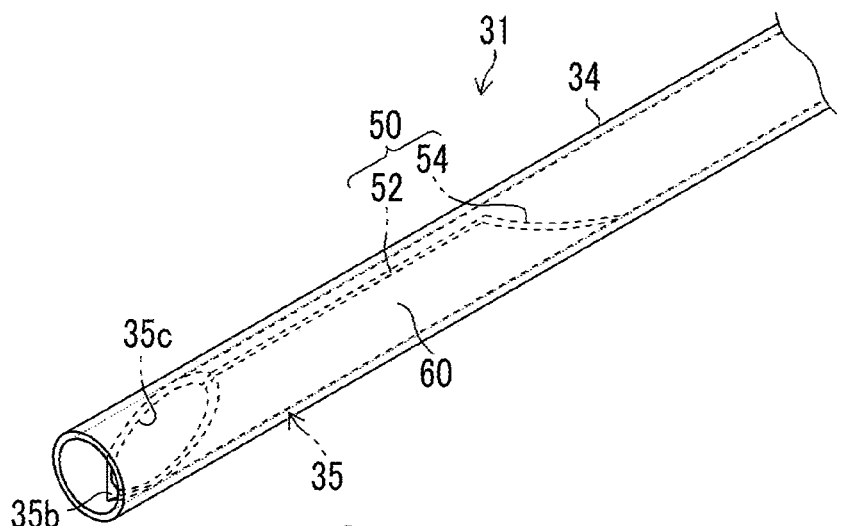
FIG. 5A is a schematic diagram showing a configuration of a distal portion of a needle tube constituting the tissue sampling device and is a view showing a state in which the distal portion of the needle tube is accommodated in a sheath.
Figure 5B:
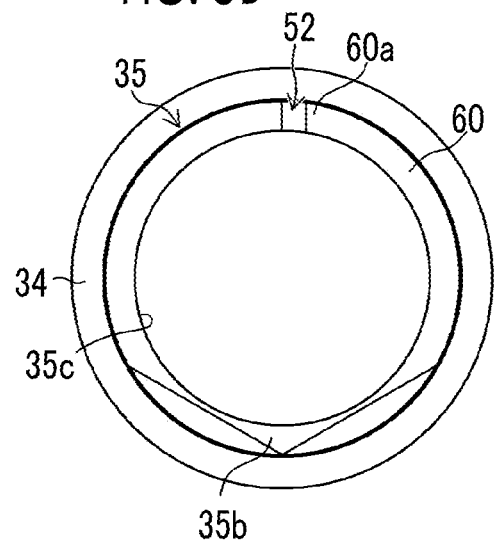
FIG. 5B is a schematic diagram showing a configuration of the distal portion of the needle tube constituting the tissue sampling device and is a view showing a state in which the distal portion of the needle tube is accommodated in the sheath.
Figure 5C:
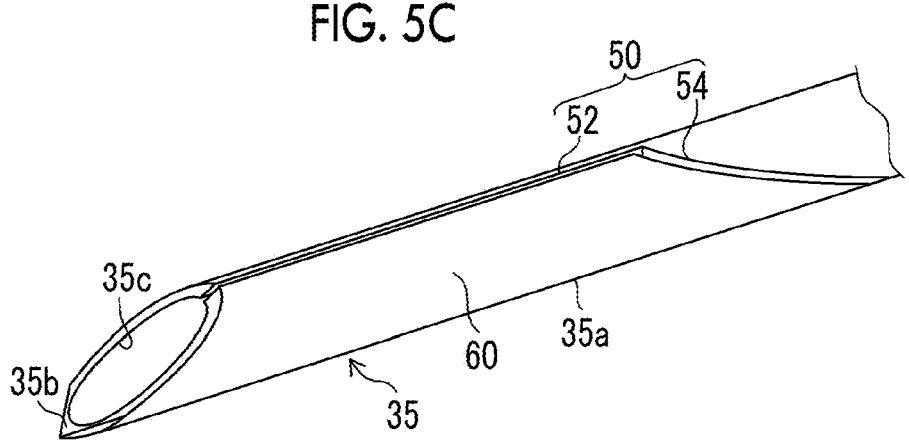
FIG. 5C is a schematic diagram showing a configuration of the distal portion of the needle tube constituting the tissue sampling device and is a view showing a state in which the distal portion of the needle tube is accommodated in the sheath.
Figure 6A:
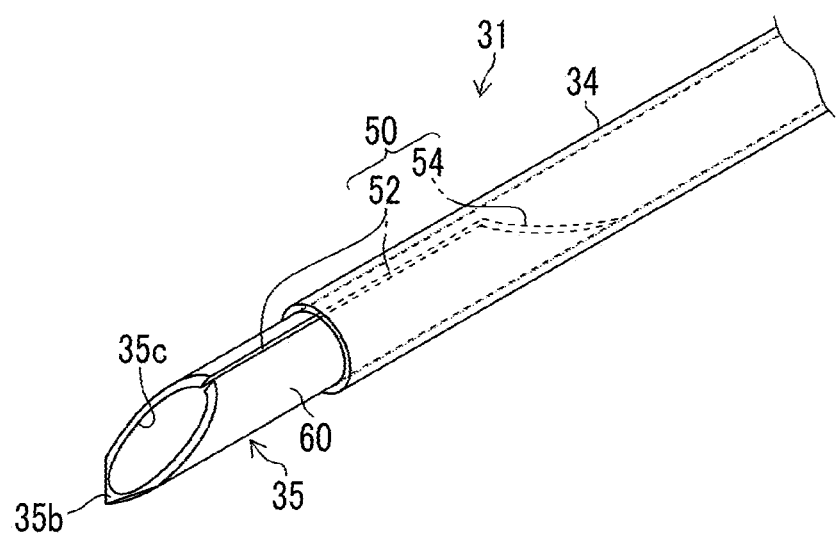
FIG. 6A is a schematic diagram showing a configuration of the distal portion of the needle tube constituting the tissue sampling device and is a view showing a state in which a part of the distal portion of the needle tube protrudes from a distal end of the sheath.
Figure 6B:
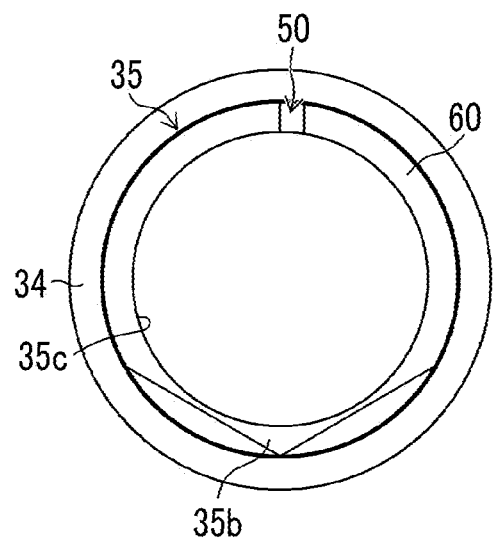
FIG. 6B is a schematic diagram showing a configuration of the distal portion of the needle tube constituting the tissue sampling device and is a view showing a state in which a part of the distal portion of the needle tube protrudes from the distal end of the sheath.
Figure 7A:
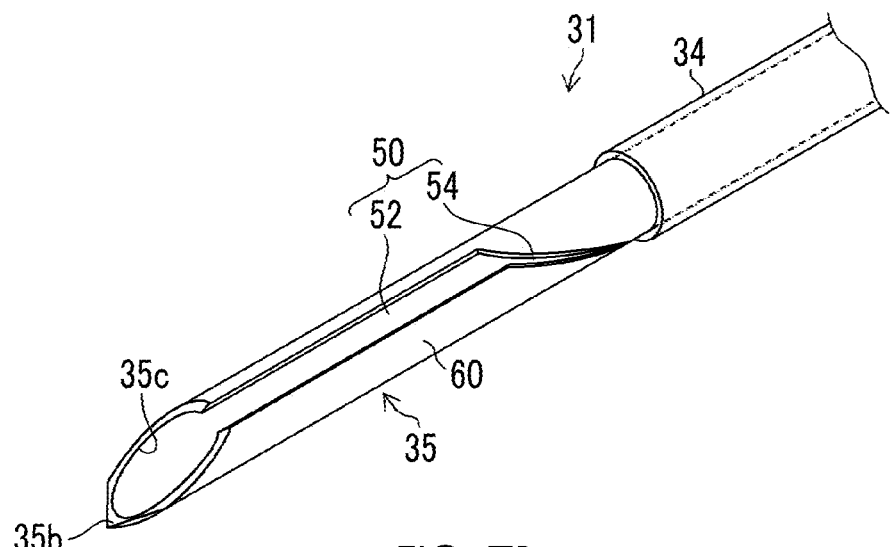
FIG. 7A is a schematic diagram showing a configuration of the distal portion of the needle tube constituting the tissue sampling device and is a view showing a state in which the entirety of the distal portion of the needle tube protrudes from the distal end of the sheath.
Figure 7B:
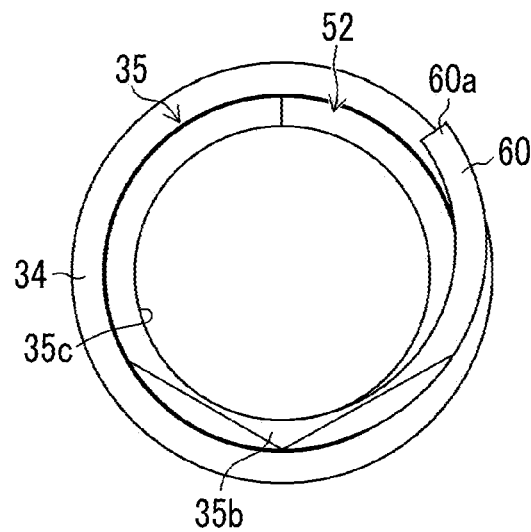
FIG. 7B is a schematic diagram showing a configuration of the distal portion of the needle tube constituting the tissue sampling device and is a view showing a state in which the entirety of the distal portion of the needle tube protrudes from the distal end of the sheath.
Figure 7C:
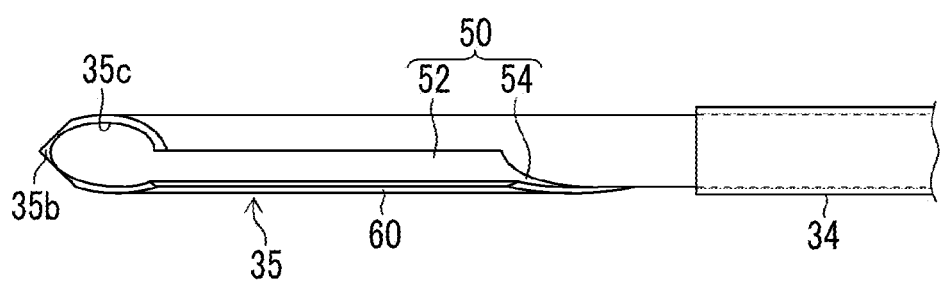
FIG. 7C is a schematic diagram showing a configuration of the distal portion of the needle tube constituting the tissue sampling device and is a view showing a state in which the entirety of the distal portion of the needle tube protrudes from the distal end of the sheath.

FIG. 5A to FIG. 7C are schematic diagrams showing the configuration of the distal portion of the insertion unit 31. FIGS. 5A to 5C are views showing states in which the distal portion of the needle tube 35 is accommodated in the sheath 34. FIG. 5A is an external perspective view, FIG. 5B is a front view when viewed from the distal side, and FIG. 5C is a perspective view in which only the needle tube 35 is extracted and shown. FIGS. 6A and 6B are views showing states in which a part of the distal portion of the needle tube 35 protrudes from the distal end of the sheath 34. FIG. 6A is an external perspective view and FIG. 6B is a front view when viewed from the distal side. FIGS. 7A to 7C are views showing states in which the distal portion of the needle tube 35 completely protrudes from the distal end of the sheath 34. FIG. 7A is an external perspective view, FIG. 7B is a front view when viewed from the distal side, and FIG. 7C is a plan view when viewed from the above.

As shown in FIGS. 5A to 7C, the distal portion of the needle tube 35 is constituted so as to be expandable and contractible when coming in and out of the distal end of the sheath 34. Specifically, an elastic piece 60 which is elastically deformable in a radial direction when coming in and out of the distal end of the sheath 34 is provided. This elastic piece 60 is a cantilever-like portion formed by a slit 50 (52, 54) to be described below, and is a portion which has been deformed (property-provided) through heat treatment or the like such that a free end portion 60a of the elastic piece is positioned further on the radially outside than the inner surface of the sheath 34 when viewed from an axial direction of the needle tube 35 (refer to FIG. 7B).

In the states in which at least a part of the distal portion of the needle tube 35 is accommodated in the sheath 34 as shown in FIGS. 5A to 6B, the elastic piece 60 is biased toward the radially inward by the sheath 34, and the distal portion of the needle tube 35 enters a state in which the diameter thereof is reduced. In contrast, in the states in which the distal portion of the needle tube 35 protrudes from the distal end of the sheath 34 as shown in FIGS. 7A to 7C, the elastic piece 60 is not restrained by the sheath 34, and therefore, the distal portion of the needle tube 35 enters a state in which the diameter thereof is enlarged radially outward.

In order to form such an elastic piece 60, a slit 50 is provided in a side portion of the distal portion of the needle tube 35. This slit 50 is constituted of a distal side slit 52 and a proximal side slit 54.

The distal side slit 52 is a thin through hole which is linearly formed along the axial direction toward the proximal side from a distal opening 35c of the needle tube 35. The shape of the distal side slit 52 is not particularly limited as long as it is possible to form the free end portion 60a of the cantilever-like elastic piece 60. For example, the distal side slit 52 may be formed along a direction in which the distal side slit is obliquely inclined at a predetermined angle with respect to the axial direction, or the distal side slit may have various arbitrary shapes such as a saw blade shape or a wave shape.

The distal side slit 52 is disposed at a position at which the phase of the distal side slit is different from that of the needle tip 35b of the needle tube 35. That is, in a case where each portion is projected on a projection plane which is perpendicular to the axial direction of the needle tube 35, the distal side slit 52 and the needle tip 35b are disposed at positions at which the distal side slit and the needle tip do not overlap each other. According to this configuration, when biological tissue is pierced with the needle tube 35, it is possible to suppress an increase in insertion resistance (puncture resistance) received from the biological tissue, thereby improving operability.

The proximal side slit 54 is a thin through hole which spirally extends in the axial direction toward the proximal side by having the end portion of the proximal side of the distal side slit 52 as a starting point. Similarly to the distal side slit 52, the shape of the proximal side slit 54 is not particularly limited as long as it is possible to form the free end portion of the cantilever-like elastic piece 60. However, it is preferable that the proximal side slit is spirally formed along the axial direction as in this example. Accordingly, when the distal portion of the needle tube 35 is accommodated in the sheath 34, biasing force which the elastic piece 60 receives from the sheath 34 toward the radially inside becomes gradually large in proportion to the length of the distal portion thereof accommodated in the sheath 34. Therefore, it is possible to smoothly and easily accommodate the distal portion of the needle tube 35 in the sheath 34. Accordingly, it is possible to hold biological tissue, which has been taken into the distal portion of the needle tube 35, in the sheath 34 in a state of being reliably captured. For this reason, it is possible to remove the insertion unit 31 from the treatment tool insertion channel 21 without falling of the sampled biological tissue in the middle of the removal.

Figure 8:
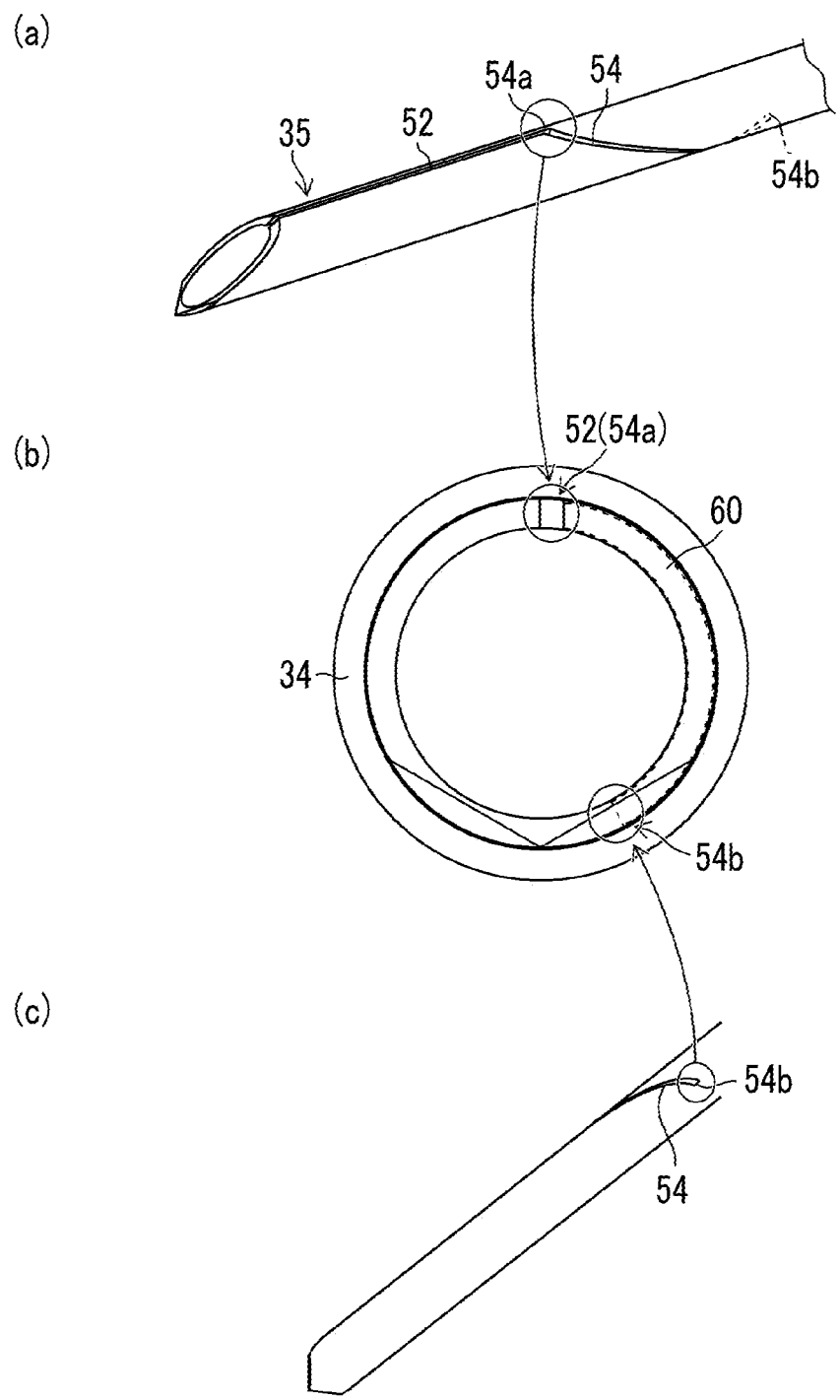
FIG. 8 is an explanatory view showing an arrangement relation between a distal opening of the needle tube, a sharp tip portion, and a proximal side slit.

Similarly to the distal side slit 52, the proximal side slit 54 is disposed at a position at which the phase of the distal side slit is different from that of the needle tip 35*b* of the needle tube 35. That is, in a case where each portion is projected on a projection plane which is perpendicular to the axial direction of the needle tube 35 as shown in the sections of (a) to (c) in FIG. 8, the proximal side slit 54 is formed in a state in which the phase of the needle tip 35*b* of the needle tube 35 is deviated so as not to be included in the range in the circumferential direction in which the proximal side slit 54 is formed. According to this configuration, even if the elastic piece 60 is expanded radially outwardly when the distal portion of the needle tube 35 protrudes from the distal end of the sheath 34, the needle tip 35*b* is not directly affected by the deformation of the elastic piece 60 and the needle tip 35*b* is at a position at which the needle tip is fixed at all times, thereby enabling stable puncturing.

Figure 9A:
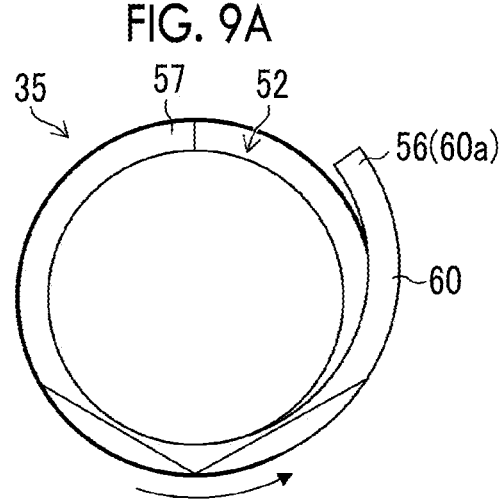
FIG. 9A is an explanatory view for illustrating a curvature radius of the needle tube.
Figure 9B:
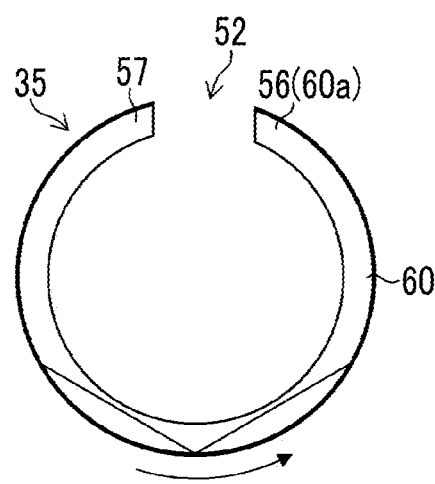
FIG. 9B is an explanatory view for illustrating a curvature radius of the needle tube.

In the present embodiment, the outer diameter of the distal portion of the needle tube 35 protruding from the distal end of the sheath 34 has two different kinds of curvature. Specifically, as shown in FIG. 9A, in edge portions 56 and 57 which are respectively provided on both sides of the distal side slit 52, the curvature radius of one edge portion 56 (free end portion 60*a* of the elastic piece) on a side on which the elastic piece 60 is provided is configured to be larger than that of the other edge portion 57. For this reason, as shown in FIG. 9B, a step is formed between the edge portions 56 and 57 in comparison to a case where the curvature radius of each of the edge portions 56 and 57 is formed to be the same as each other. Accordingly, when the needle tube 35 is rotated counterclockwise (that is, from a side on which the curvature radius is small to a side on which the curvature radius is large) in the drawing, it is possible to sample a larger amount of biological tissue through the gap formed in this step.

The present embodiment is configured as described above. Next, a method for sampling biological tissue using this tissue sampling device 30 will be described.

First, the distal portion main body 12 of the ultrasonic endoscope is disposed at a predetermined position with respect to the body cavity inner wall S. In this state, when a tissue sampling site in the body is captured within an observation visual field of the ultrasonic transducer unit 16 constituting the ultrasonic observation portion 14, the insertion unit 31 is inserted into the treatment tool insertion channel 21 and the distal portion of the insertion unit 31 is positioned in the vicinity of the distal end of the treatment tool lead-out portion 18. In addition, the syringe 33 is connected to the luer lock portion 44. A syringe for suction is used as this syringe 33.

Figure 10A:
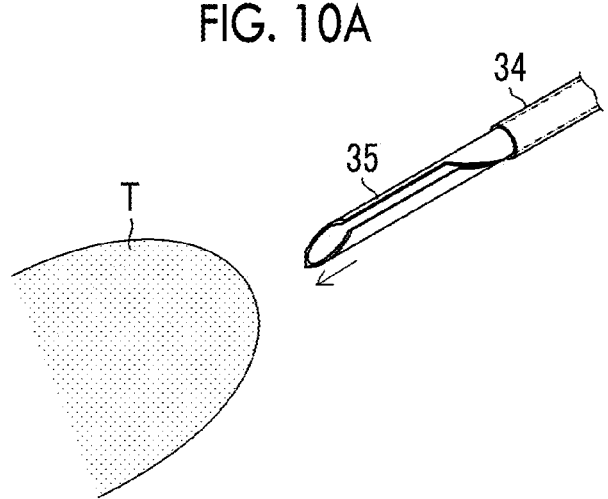
FIG. 10A is an explanatory view showing a method of sampling biological tissue using the tissue sampling device.

Here, the distal portion of the needle tube 35 in the insertion unit 31 which is in a state before being inserted into the body cavity inner wall S is covered by the sheath 34. In this state, the distal portion of the needle tube 35 is made to protrude from the distal end of the sheath 34 as shown in FIG. 10A by operating the slider 41 in the operating unit 32 so as to be pushed into the casing 40. Accordingly, the distal portion of the needle tube 35 enters a state in which the diameter thereof is enlarged, and therefore, the volume of the lumen in the distal portion thereof increases. Then, the needle tip 35*b* in the distal portion of the needle tube 35 is pierced into the body from the body cavity inner wall S in the state in which the diameter of the distal portion thereof is enlarged.

The piercing route of this needle tube 35 into the body can be captured within the ultrasonic observation visual field. Therefore, it is possible to accurately and easily perform a piercing operation and to reliably shoot at the tissue sampling site T.

Figure 10B:
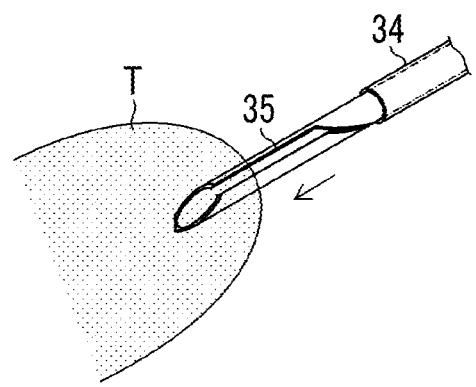
FIG. 10B is an explanatory view showing the method of sampling biological tissue using the tissue sampling device.

As shown in FIG. 10B, if the needle tip 35*b* of the needle tube 35 progresses to advance to the biological tissue sampling site T, the syringe 33 is operated to make the pressure of the inside of the needle tube 35 negative. Due to the action of this negative pressure, biological tissue is incorporated into the needle tube 35 from the distal opening 35*c* of the needle tube 35 and is sampled within the needle tube 35. The operation performed when sampling biological tissue within the needle tube 35 is not limited thereto. For example, biological tissue may be sampled by simply piercing the biological tissue with the needle tube 35 without applying negative pressure to the needle tube 35. Alternately, the pressure in the needle tube 35 may be repeatedly shifted between negative pressure and positive pressure using the syringe 33 in a state in which the needle tip 35*b* of the needle tube 35 is made to advance to the biological tissue sampling site T, and at that time, biological tissue may be reliably sampled within the needle tube 35 through an operation of changing the direction of the needle tip 35*b* of the needle tube 35 or the like.

Figure 10C:
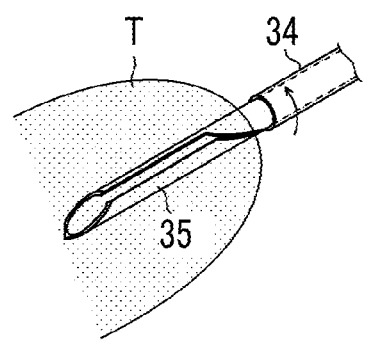
FIG. 10C is an explanatory view showing the method of sampling biological tissue using the tissue sampling device.
Figure 10D:
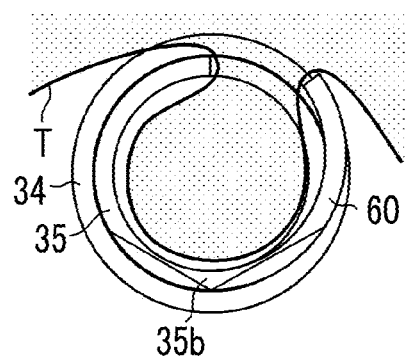
FIG. 10D is an explanatory view showing the method of sampling biological tissue using the tissue sampling device.

The biological tissue sampling site T is pierced with the needle tip 35*b* of the needle tube 35 which is then rotated using the operating unit 32 as shown in FIG. 10C. Here, the outer diameter of the distal portion of the needle tube 35 has two different kinds of curvature and a step is formed in both edge portions of the distal side slit 52. Therefore, as shown in FIG. 10D, when the needle tube 35 is rotated, a large amount of biological tissue are taken by the distal portion of the needle tube 35 through the gap formed in this step.

Figure 10E:
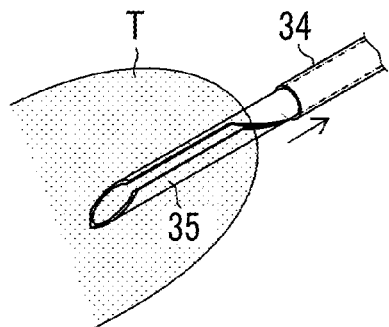
FIG. 10E is an explanatory view showing the method of sampling biological tissue using the tissue sampling device.
Figure 10F:
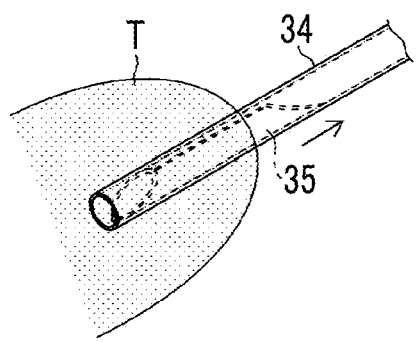
FIG. 10F is an explanatory view showing the method of sampling biological tissue using the tissue sampling device.
Figure 10G:
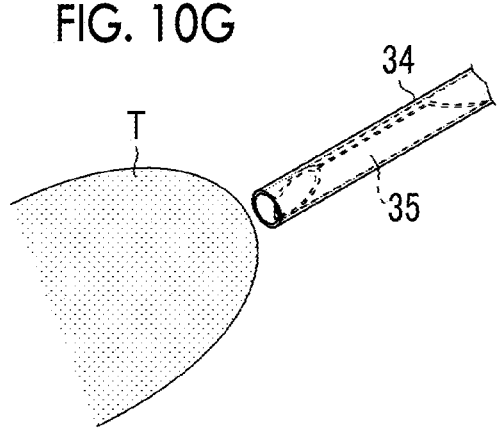
FIG. 10G is an explanatory view showing the method of sampling biological tissue using the tissue sampling device.

As described above, after the biological tissue is sampled using the insertion unit 31 of the tissue sampling device 30, the insertion unit 31 is taken out of the treatment tool insertion channel 21. At this time, the insertion unit 31 is taken out of the treatment tool insertion channel 21 in a state in which the distal portion of the needle tube 35 is made to protrude from the distal end of the sheath 34 as shown in FIG. 10E. The operation performed when taking out the insertion unit 31 from the treatment tool insertion channel 21 is not limited thereto. For example, the insertion unit 31 may be taken out of the treatment tool insertion channel 21 as shown in FIG. 10G after the sheath 34 is made to advance to the biological tissue sampling site T and the distal portion of the needle tube 35 is accommodated in the sheath 34 as shown in FIG. 10F. In this case, it is possible to take out the insertion unit 31 from the treatment tool insertion channel 21 in a state in which the biological tissue which has been accommodated in the sheath 34 and sampled in the distal portion of the needle tube 35 is reliably captured.

After taking out the insertion unit 31 from the treatment tool insertion channel 21, a syringe for feeding, for example, a formalin liquid is connected to the luer lock portion 44 instead of the syringe for suction, and the formalin liquid is fed to the needle tube 35 from this syringe. Accordingly, it is possible to transfer the sampled tissue to a test tube or the like.

As described above, according to the present embodiment, the distal portion of the needle tube 35 is configured so as to be expandable and contractible when coming in and out of the distal end of the sheath 34. Therefore, it is possible to easily sample a sufficient amount of biological tissue for performing diagnosis for a pathological confirmation. In addition, the outer diameter of the distal portion of the needle tube 35 in a state of protruding from the distal end of the sheath 34 has two different kinds of curvature and a step is formed in both of the edge portions 56 and 57 of the distal side slit 52. Therefore, it is possible to sample a larger amount of biological tissue through the gap formed in the step, through an operation of rotating the needle tube 35 which has been pierced into the biological tissue.

In the above, the tissue sampling device according to the present invention has been described in detail, but the present invention is not limited to the example described above. As a matter of course, various improvements or modifications may be performed within a range not departing from the gist of the present invention. Hereinafter, several modification examples will be described.

First Modification Example

Figure 11:
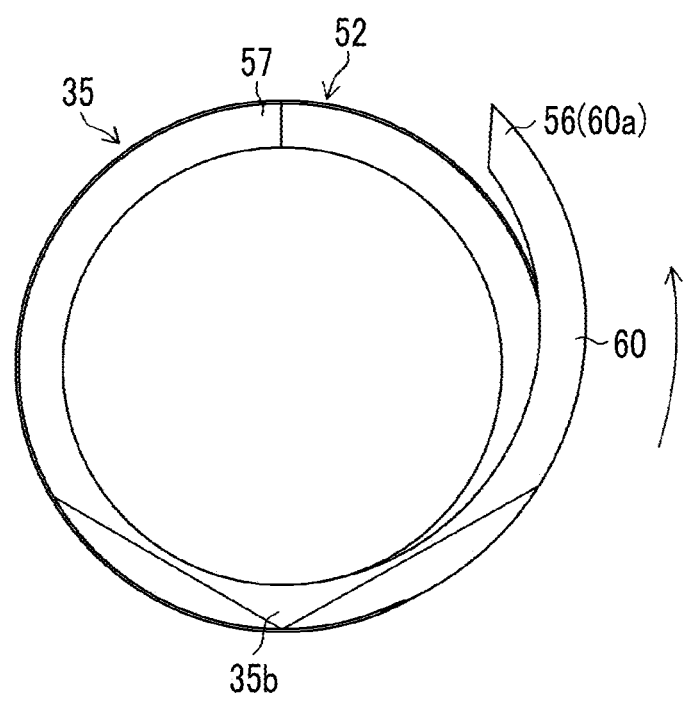
FIG. 11 is a front view showing a distal portion of a needle tube according to a first modification example.

In a first modification example shown in FIG. 11, one edge portion 56 (free end portion 60a of the elastic piece 60) out of both edge portions 56 and 57 of a distal side slit 52 formed in a distal portion of a needle tube 35 is formed in a blade shape (edge shape) with a tapered sharp tip. According to this configuration, when the needle tube 35 is rotated counterclockwise in the drawing, it is possible to easily cut biological tissue which has been taken into the needle tube 35.

Second Modification Example

Figure 12:
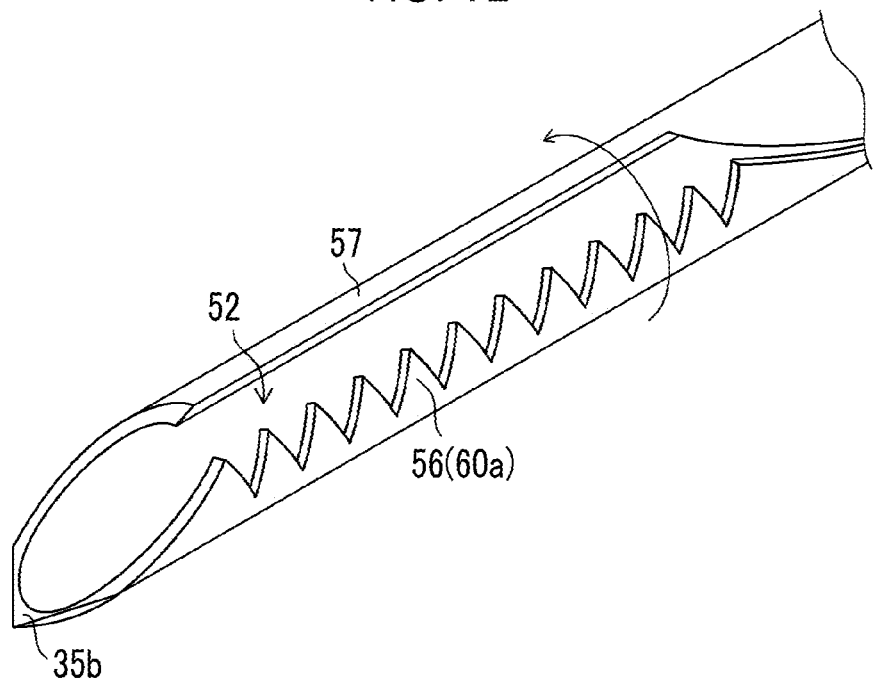
FIG. 12 is a perspective view showing a distal portion of a needle tube according to a second modification example.

In a second modification example shown in FIG. 12, one edge portion 56 (free end portion 60a of the elastic piece 60) out of both edge portions 56 and 57 of a distal side slit 52 formed in a distal portion of a needle tube 35 is formed in a saw blade shape. According to this configuration, similarly to the first modification example, when the needle tube 35 is rotated in the direction shown by an arrow in the drawing, it is possible to easily cut biological tissue which has been taken into the needle tube 35.

Third Modification Example

Figure 13A:
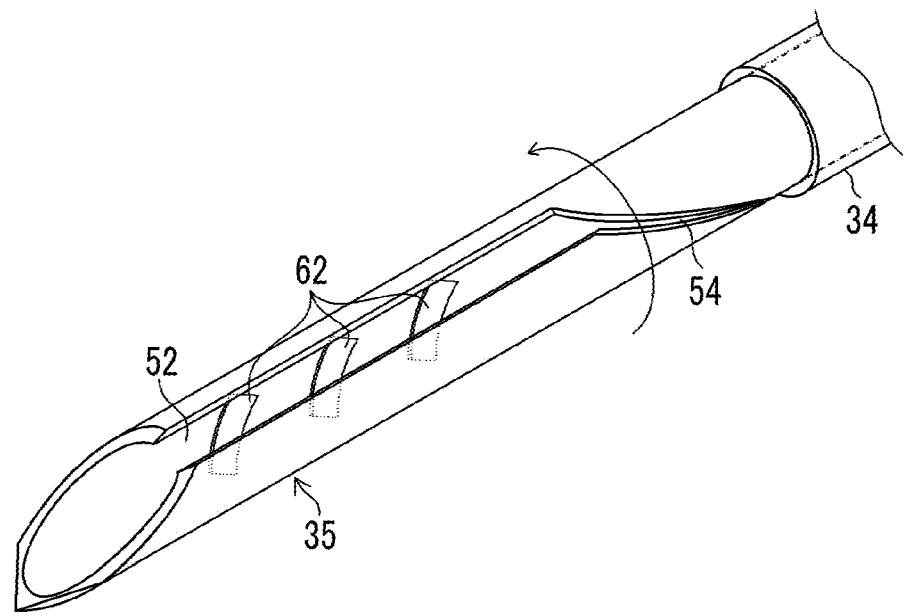
FIG. 13A is a perspective view showing a distal portion of a needle tube according to a third modification example.
Figure 13B:
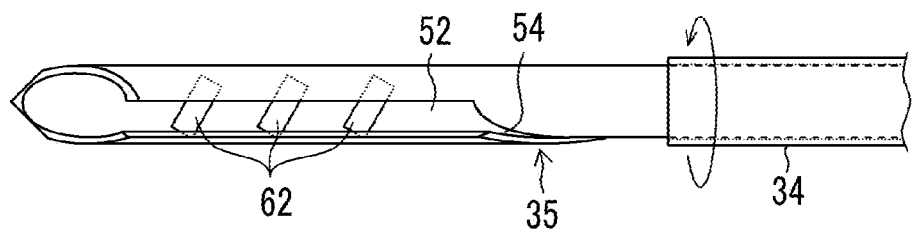
FIG. 13B is a plan view showing the distal portion of the needle tube according to the third modification example.

In a third modification example shown in FIGS. 13A and 13B, one or a plurality of guide members 62 are provided on an inner surface of a distal portion of a needle tube 35. This guide member 62 is protrusively provided in a state of being inclined in an oblique direction with respect to an axial direction. When the needle tube 35 is rotated in a direction shown by an arrow in the drawing, biological tissue which has been taken into the needle tube 35 is guided to a proximal side of the needle tube 35, and therefore, it is possible to sample a larger amount of biological tissue.

Fourth Modification Example

Figure 14:
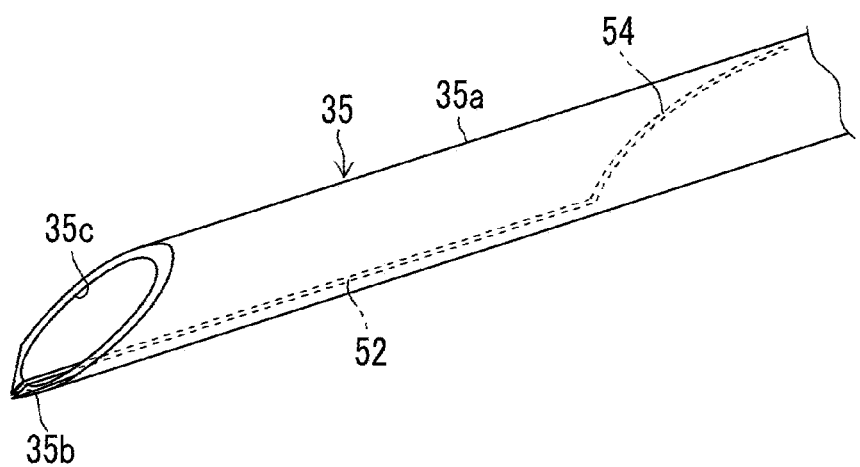
FIG. 14 is a perspective view showing a distal portion of a needle tube according to a fourth modification example.

In a fourth modification example shown in FIG. 14, a distal side slit 52 and a proximal side slit 54 are formed such that the phases thereof are different from those in the present embodiment by 180 degrees. That is, the linear distal side slit 52 is formed in a distal portion of a needle tube 35 along an axial direction from a needle tip 35b as a sharp tip portion which is positioned at the most distal end in a distal opening 35c, and the spiral slit 54 is formed on a proximal side thereof. According to this configuration, when biological tissue is pierced with the needle tube 35, the diameter of the distal portion of the needle tube 35 is further enlarged due to insertion resistance received from the biological tissue, and therefore, it is possible to obtain an effect in which the amount of biological tissue sampled can be increased.

Fifth Modification Example

Figure 15:
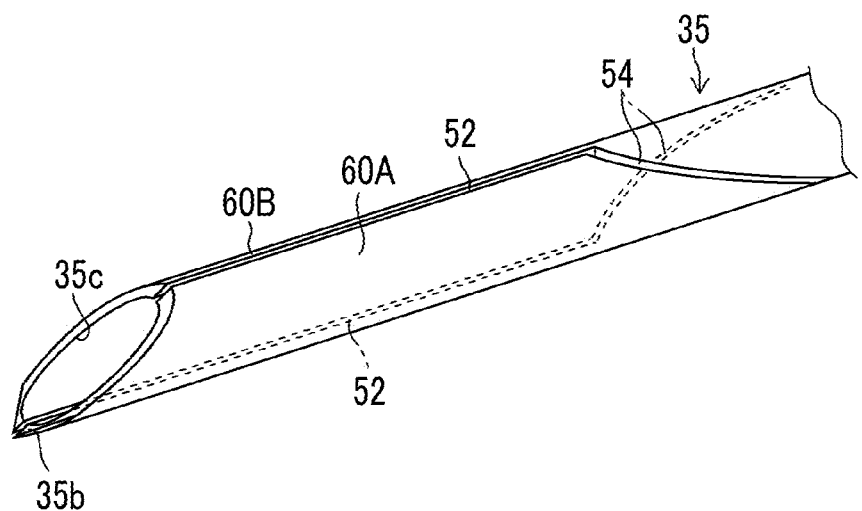
FIG. 15 is a perspective view showing a distal portion of a needle tube according to a fifth modification example.
Figure 16:
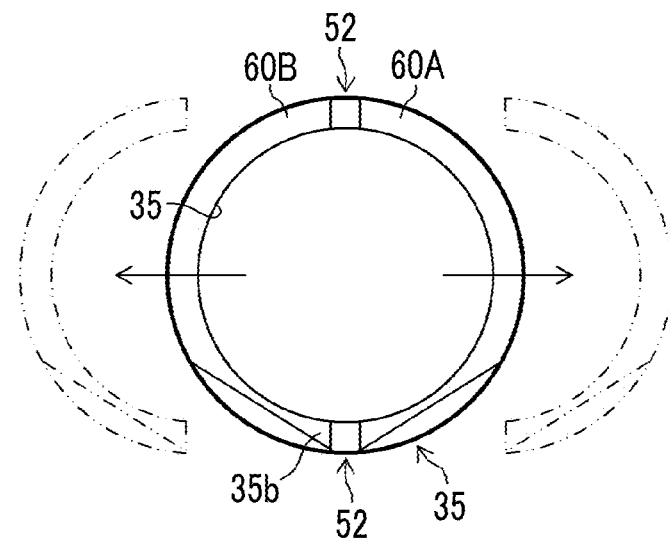
FIG. 16 is a front view showing the distal portion of the needle tube according to the fifth modification example.

A fifth modification example shown in FIG. 15, is an example in which the present embodiment and the fourth modification example are combined. That is, two sets of distal side slits 52 and proximal side slits 54 are provided in a distal portion of a needle tube 35, and two elastic pieces 60A and 60B are provided due to these slits 52 and 54. According to this configuration, when the distal portion of the needle tube 35 protrudes from a distal end of a sheath 34 as an imaginary line shown in FIG. 16, the diameters of the elastic pieces 60A and 60B are enlarged in directions of away from each other. Therefore, it is possible to sample a larger amount of biological tissue compared to the aspect in which one elastic piece 60 is provided.

EXPLANATION OF REFERENCE

10: insertion unit
11: angle portion
12: distal portion main body
13: endoscopic observation portion
14: ultrasonic observation portion
21: treatment tool insertion channel
30: tissue sampling device
31: insertion unit
32: operating unit
33: syringe
34: sheath
35: needle tube
35a: main body pipe
35b: needle tip
35c: distal opening
50: slit
52: distal side slit
54: proximal side slit
60: elastic piece
60a: free end portion
56: edge portion
57: edge portion
62: guide member

What is claimed is:

1. A tissue sampling device comprising:
a flexible sheath;
a needle tube which is inserted into the sheath so as to advance and retreat where the needle tube is configured to puncture biological tissue; and
an operating unit which is provided on a proximal side of the sheath and is used to move the needle tube back and forth, comprising a casing and a slider slidably disposed in the casing, wherein the sheath is fixed to the casing, the slider is fixed to the needle tube, and the slider is adapted to slide relative to the casing so as to operate back and forth movement of the needle tube relative to the flexible sheath, wherein the needle tube has a distal portion provided with a slit extending toward a proximal side of the needle tube from a distal opening, and when the distal portion is in a state of protruding from a distal end of the sheath, at least a part of the distal portion is positioned radially outside of an inner surface of the sheath when viewed from an axial direction of the needle tube, wherein a distal side of the slit comprises a linear portion which is linearly formed along the axial direction of the needle tube toward the proximal side of the needle tube from the distal opening of the needle tube, and a proximal portion of the same slit is formed in a spiral shape with respect to the axial direction of the needle tube, wherein the linear portion of the slit is formed on only one side of the needle tube, wherein the linear portion of the slit is parallel to the axial direction of the needle tube from the distal opening of the needle tube to the proximal portion of the slit, and the proximal portion of the slit extends from a proximal end of the linear portion of the slit toward the proximal side of the needle tube, wherein the slit extends toward the proximal side of the needle tube from a portion other than a sharp tip portion of the distal opening of the needle tube, and the linear portion of the slit expands uniformly in order that the linear portion of the slit has a constant width upon protruding fully from the sheath.

2. The tissue sampling device according to claim 1, wherein the distal portion of the needle tube is biased in a direction in which a curvature radius of at least one of edge portions of the needle tube facing each other across the slit is enlarged.

3. The tissue sampling device according to claim 1, wherein the slit comprises a plurality of slits, the slits are provided in the distal portion of the needle tube.

4. The tissue sampling device according to claim 1, wherein a diameter of the distal portion of the needle tube is made to be less than or equal to an inner diameter of the sheath when the distal portion thereof is accommodated in the sheath.

* * * * *